United States Patent [19]

Perdelwitz, Jr., Lee E. et al.

[11] Patent Number: 4,961,930
[45] Date of Patent: Oct. 9, 1990

[54] PET PAD OF THERMOPLASTIC CONTAINING MATERIALS WITH INSECTICIDE

[75] Inventors: Perdelwitz, Jr., Lee E., Tacoma; Robert H. Young, Maple Valley; Earl D. Hasenwinkle; Ron H. Iff, both of Puyallup; Amar H. Neogi, Seattle, all of Wash.

[73] Assignee: Weyerhaeuser Company, Tacoma, Wash.

[21] Appl. No.: 188,291

[22] Filed: Apr. 29, 1988

[51] Int. Cl.⁵ .................................................. A61K 9/70
[52] U.S. Cl. .................................... 424/411; 428/283; 428/284; 428/288; 428/402; 428/192; 428/913
[58] Field of Search ............... 428/283, 288, 284, 402, 428/913, 192; 424/411; 106/15.05

[56] References Cited

U.S. PATENT DOCUMENTS

| | | | |
|---|---|---|---|
| 30,972 | 6/1882 | Kyle et al. | |
| 247,368 | 2/1878 | Whitehead | 128/287 |
| 253,674 | 12/1879 | Whitehead | 128/287 |
| 254,097 | 2/1880 | Richards | 128/287 |
| 254,098 | 2/1880 | Richards | 128/287 |
| 254,099 | 2/1880 | Richards | 128/287 |
| 272,190 | 1/1884 | Sneider | 604/362 |
| 276,073 | 10/1884 | Whitehead | 128/287 |
| 1,442,056 | 1/1923 | Edmonds | |
| 2,652,183 | 9/1953 | Hlivka | 227/49 |
| 2,788,003 | 4/1957 | Morin | |
| 2,990,101 | 6/1961 | Mead et al. | 229/53 |
| 3,016,599 | 1/1962 | Perry | |
| 3,065,751 | 11/1962 | Gobbo, Sr. et al. | 128/287 |
| 3,315,676 | 4/1967 | Cooper | 128/287 |
| 3,405,031 | 11/1968 | Sisson | 162/198 |
| 3,441,468 | 3/1969 | Siggel et al. | 128/284 |
| 3,477,433 | 11/1969 | Dillon | 128/290 |
| 3,501,369 | 3/1970 | Drelich et al. | 161/150 |
| 3,542,634 | 11/1970 | Such et al. | 161/88 |
| 3,556,936 | 1/1971 | Miyamoto | |
| 3,570,491 | 3/1971 | Sneider | 128/290 |
| 3,591,875 | 7/1971 | Zipf, III et al. | 5/334 |
| 3,706,626 | 2/1972 | Smith et al. | 161/37 |
| 3,717,150 | 2/1973 | Schwartz | 128/284 |
| 3,765,997 | 10/1973 | Dunning | 161/171 |
| 3,767,452 | 10/1973 | Lauchenauer | 117/37 R |
| 3,809,606 | 5/1974 | Stansbrey | 162/194 |
| 3,877,974 | 4/1975 | Mischutin | 428/290 |
| 3,881,490 | 5/1975 | Whitehead et al. | 128/289 |
| 3,888,248 | 6/1975 | Moore et al. | 161/169 |
| 3,891,157 | 6/1975 | Justus | 242/56.2 |
| 3,903,890 | 9/1975 | Mesek et al. | 604/379 |
| 3,927,673 | 12/1975 | Taylor | 128/132 |

(List continued on next page.)

FOREIGN PATENT DOCUMENTS

| | | |
|---|---|---|
| 974107 | 9/1975 | Canada . |
| 202472A | 11/1986 | European Pat. Off. . |
| 2516373 | 4/1975 | Fed. Rep. of Germany . |
| 1326915 | 11/1970 | United Kingdom . |
| 2061339 | 10/1980 | United Kingdom . |

OTHER PUBLICATIONS

National Highway Traffic Safety Administration DOT Regulations 49 CFR Sections 571.213 and 571.302.
Brochure "GGT and Gerber Camsco . . . Automation Technology for the Furniture Industry".

*Primary Examiner*—James J. Bell
*Attorney, Agent, or Firm*—Klarquist, Sparkman, Campbell, Leigh & Whinston

[57] ABSTRACT

Pet pads contain insecticide and have at least one layer comprising a mixture of thermoplastic and other fibers. This latter layer may be thermobonded together and then densified along at least a section of the eventual peripheral edge margin of a pet pad to be formed from the material. By including insecticide in the mixture prior to thermobonding, the insecticide is fixed in the pad during thermobonding. Thermoplastic material-containing cover sheets may also be secured to the core and densified along the periphery of the pad. The entire eventual peripheral edge margin of the pet pad is typically densified. The densified edge acts as a partial liquid barrier and also helps retain the insecticide in the pad, especially if the insecticide is not fixed by thermobonding.

15 Claims, 3 Drawing Sheets

U.S. PATENT DOCUMENTS

| | | | |
|---|---|---|---|
| 3,934,285 | 1/1976 | May | 117/137 |
| 3,971,381 | 7/1976 | Gibson . | |
| 3,996,825 | 12/1976 | Terry | 83/53 |
| 4,047,534 | 9/1977 | Thomaschefsky et al. | 128/461 |
| 4,078,124 | 3/1978 | Prentice . | |
| 4,079,739 | 3/1978 | Whitehead | 128/290 R |
| 4,082,886 | 3/1978 | Butterworth et al. | 428/284 |
| 4,100,324 | 7/1978 | Anderson et al. | 428/288 |
| 4,129,132 | 12/1978 | Butterworth et al. | 128/287 |
| 4,160,059 | 7/1979 | Samejima | 428/288 |
| 4,170,680 | 10/1979 | Cumbers | 428/195 |
| 4,182,170 | 1/1980 | Grupp | 83/177 |
| 4,196,245 | 4/1980 | Kitson et al. | 428/198 |
| 4,213,459 | 7/1980 | Sigl et al. | 128/284 |
| 4,257,842 | 3/1981 | Ciaccia et al. | 162/117 |
| 4,275,105 | 6/1981 | Boyd et al. | 428/198 |
| 4,286,030 | 8/1981 | Moore | 429/253 |
| 4,289,580 | 9/1981 | Elston et al. . | |
| 4,296,168 | 10/1981 | Ambrose | 428/288 |
| 4,315,965 | 2/1982 | Mason et al. | 428/198 |
| 4,333,979 | 6/1982 | Sciaraffa et al. . | |
| 4,381,783 | 5/1983 | Elias | 604/368 |
| 4,425,126 | 1/1984 | Butterworth et al. | 604/366 |
| 4,425,130 | 1/1984 | DesMarais | 128/156 |
| 4,429,001 | 1/1984 | Kolpin et al. | 428/283 |
| 4,443,512 | 4/1984 | Delvaux | 428/162 |
| 4,458,042 | 7/1984 | Espy | 524/14 |
| 4,488,928 | 2/1984 | Khan et al. . | |
| 4,493,868 | 1/1985 | Meitner . | |
| 4,500,580 | 2/1985 | Luciani | 428/43 |
| 4,525,409 | 6/1985 | Elesh | 428/193 |
| 4,525,410 | 6/1985 | Hagiwara et al. | 424/411 |
| 4,548,856 | 10/1985 | Khan et al. . | |
| 4,573,986 | 3/1986 | Minetola et al. | 604/366 |
| 4,578,071 | 3/1986 | Buell | 604/379 |
| 4,609,580 | 9/1986 | Rockett et al. | 428/198 |
| 4,619,862 | 11/1986 | Sokolowski et al. | 428/221 |
| 4,620,466 | 11/1986 | Jumel et al. | 83/177 |
| 4,629,457 | 12/1986 | Ness | 604/382 |
| 4,647,497 | 3/1987 | Weeks | 428/284 |
| 4,650,481 | 3/1987 | O'Connor et al. | 604/380 |
| 4,655,877 | 4/1987 | Horimoto et al. . | |
| 4,751,134 | 6/1988 | Chenoweth et al. | 428/284 |
| 4,752,349 | 6/1988 | Gebel | 156/267 |
| 4,769,023 | 9/1988 | Goebel et al. | 604/385 R |

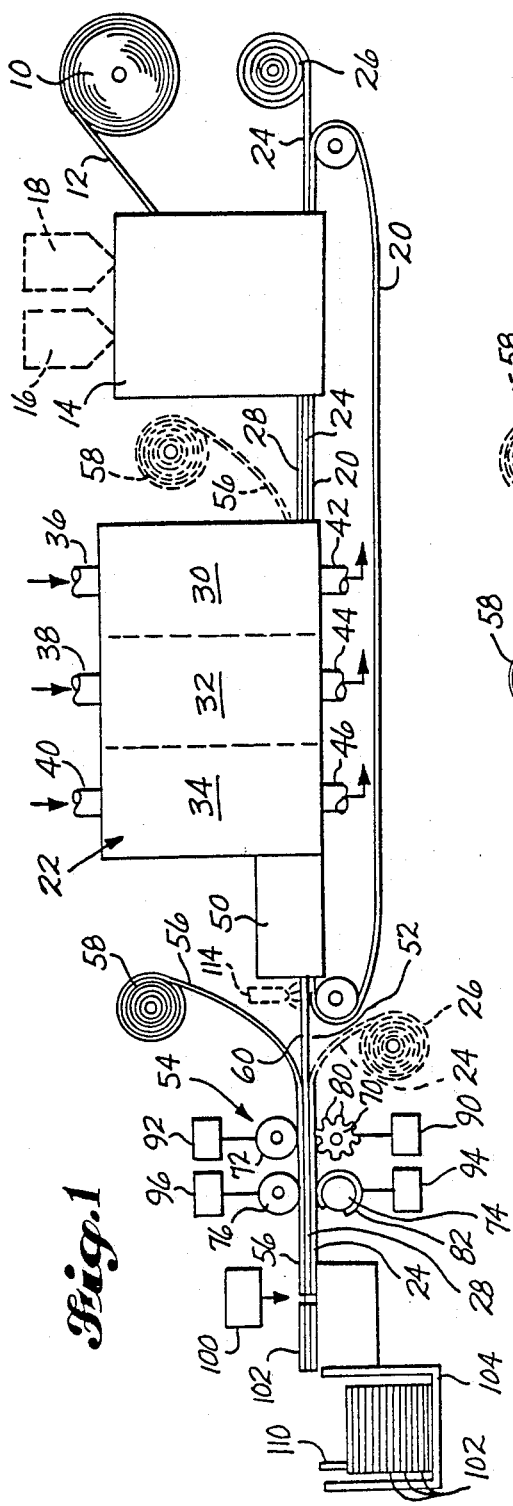
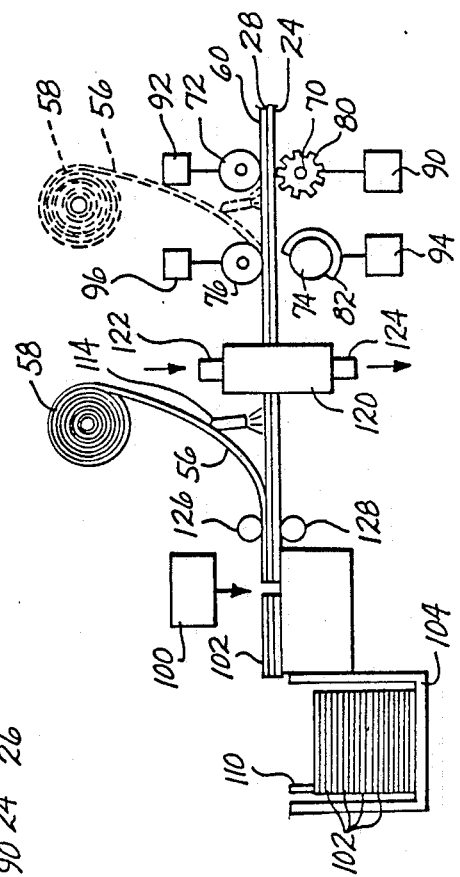

PET PAD OF THERMOPLASTIC CONTAINING MATERIALS WITH INSECTICIDE

BACKGROUND OF THE INVENTION

1. Technical Field

The present invention relates to single or multiple layer composite pet pads which include at least one layer formed from a mixture of thermoplastic and other nonthermoplastic fibers, such as wood pulp fibers and an insecticide.

2. Description Of The Prior Art

Articles and materials formed of a combination of thermoplastic and other fibers, such as wood pulp fibers, are known. However, these prior articles suffer from a number of disadvantages and are not known to comprise pet pads which include insecticides.

U.S. Pat. No. 4,458,042 of Espy discloses an absorbent material comprised of a consolidated blend consisting essentially of wood pulp fluff and wetting agent treated spurted polyolefin pulp. Representative polymers for the spurted polyolefin pulps include polyethylene, polypropylene and copolymers of ethylene and propylene. Mixtures of two or more of these polymers are also described as a suitable polyolefin pulp. The polyolefin pulp and wood pulp are blended, formed into a fluff pad and then consolidated by heating to a temperature above the melting point of the polyolefin pulp.

Although useful, absorbent materials formed in this manner tend to lose fibers from their outer edges, particularly when shaken. In addition, pads of these consolidated materials have a relatively low Z direction tensile strength which makes them relatively easy to pull apart, especially at the peripheral edges and by a pet. Also, pads of these materials do not impede the leakage of urine or other liquids deposited on these materials from their outer edges. Furthermore, Espy does not have or suggest the inclusion of insecticides for killing fleas, lice, mites and other pests.

U.S. Pat. No. 4,609,580 of Rockett et al. discloses an absorbent floor mat comprising a combination of a nonwoven liquid permeable wear surface, such as of nylon, an absorbent coform inner layer of a mixture of polymeric microfibers and wood pulp, and a liquid impervious film backing layer. Intermittent bonds within the periphery or field of the floor mat are provided. These bonds are formed by a patterned application of sonic energy or heat and pressure.

The absorbent layer of Rockett et al. is stated to have a basis weight in the range of from about 100–500 g/m$^2$ and preferably in the range of about 150–250 g/m$^2$. The absorbent layer is described in this patent as preferably being formed in accordance with the "coform" process described in U.S. Pat. No. 4,100,324 of Anderson et al. In the Anderson coform approach, streams of molten polymer are deposited in an airstream and combined by a secondary air stream containing, for example, wood pulp fibers. A combination of the air streams causes the distribution of the wood pulp in the microfiber matrix. Staple fibers, such as polyester, polyolefins, polyamides and mixtures thereof, can also be included. Finally, the liquid impermeable surface is described as preferably being a film with examples being thermoplastic polymers such as polyolefins, polyesters and the like, including polyethylene or polypropylene films. The film is described as being applied as a separate layer, coextruded, or coated onto the absorbent web. Calendering the exposed absorbent surface or providing a bottom adhesive layer are described as alternate ways of achieving liquid imperviousness of the underside of the floor mat.

In forming an absorbent layer in the manner of U.S. Pat. No. 4,100,324 of Anderson et al., the meltblown microfibers are softened, but are not above their melting point when they are engaged by wood pulp or the "other" fibers. Consequently, the bonding that occurs between these microfibers and the "other" fibers is relatively weak in comparison to the bonding that results when a thermobonding approach is used. Thermobonding in this sense means raising the temperature of a mixture of thermoplastic and other fibers to a temperature which is above a melt point of at least one of the thermoplastic fibers in the mixture. When this happens, a much stronger fusing of the mixture results. This makes the pad more resistant to tearing by a pet. In addition, by relying on field bonds to secure the floor mat together, the Z direction tensile strength of the Rockett et al. composite mat is relatively weak. Moreover, the peripheral edges of the Rockett et al. floor mat are as weak as the interior areas of the mat and would not impede the leakage of liquid from these edges. In addition, Rockett et al. does not suggest the inclusion of an insecticide for pest control.

Another example of a pad which exemplifies the prior art is described in U.S. Pat. No. 4,650,481 of O'Connor et al. The pad of O'Connor et al. has a liquid impermeable backing sheet, an overlaying liquid permeable face sheet and an absorbent coform layer between the backing and face sheets. The interior of the pad is provided with a quilted pattern of compression lines described as being formed by ultrasonic bonding, heat and compression or the use of glue and compression. In an illustrated example, the pad is generally rectangular and the quilting lines appear to form a pattern of squares on the pad. The backing sheet is described as being generally bonded to the absorbent material by adhesive.

The coform absorbent material of the O'Connor et al. patent is described as being of meltable polymers and staple fibers formed as disclosed in U.S. Pat. No. 4,100,324 of Anderson et al. Typical polymers are described as polyethylene, polyesters, nylon and other thermoplastic fibers. Staple fibers are described as including cotton, polyester, rayon, and nylon. A combination of polypropylene meltblown fibers and wood pulp fibers is described as preferred in any desired ratio, but preferably with meltblown polypropylene fibers being present in an amount from between about 30% and about 40% by weight of the mixture. Examples of the backing sheet in O'Connor et al. include polymer films, such as copolymers of ethylene and vinyl acetate, nylon and polyesters. The preferred backing sheet films are identified in this patent as being of polyethylene or polypropylene and a composite of polypropylene and a lightweight spun bonded fabric. Spunbonded polypropylene is listed in this patent as one example of a facing sheet.

During one method of manufacturing the O'Connor, et al. pad, the facing sheet is placed on a foraminous belt with meltblown polypropylene and wood fibers being deposited onto the facing sheet as it moves below meltblown producing nozzles. The coform thus becomes mechanically attached to the facing sheet. The combined coform and facing sheet is brought in contact with an adhesively coated polymer backing sheet which is secured to the coform side of the combination. The pad is then embossed to form the quilting pattern.

The O'Connor et al. patent suffers from many of the drawbacks of the Rockett et al. floor mat discussed above. For example, coform provides relatively weak bonding of a pad. In addition, there is a tendency of the pad of O'Connor et al. to leak at the edges. O'Connor, et al. recognizes this and describes an embodiment (FIGS. 6 and 7) directed toward solving this problem. In this embodiment, the absorbent material is centered but does not extend completely to the peripheral edge of the pad. Instead, the facing and backing sheets are directly connected at the edge of the pad. Moreover, O'Connor does not suggest the inclusion of an insecticide in such a pad.

Therefore, although thermoplastic fibers have been combined with other fibers and used in the manufacture of articles, a need exists for improved materials and articles of this type and for pet pads of such materials which include an insecticide.

SUMMARY OF THE INVENTION

In accordance with one aspect of the present invention, a mixture comprised of fibers of at least one thermoplastic material and other fibers, such as wood pulp fibers and insecticide, is thermobonded together by heating the mixture to a temperature above the melting point of the fibers of at least one thermoplastic material in the mixture. The thermobonding assists in fixing the insecticide in the pad so that it does not tend to migrate into the environment. Also, a stronger, more durable pet pad is provided. The mixture may be deposited on a traveling foraminous belt and passed through a pull-through hot air thermobonder to supply the heat for thermobonding purposes. The resulting web or sheet is used to form pads or other articles or the core for laminated articles.

The thermobonded mixture is compressed and densified along at least a section of the eventual peripheral edge margin of the article. The densified edge also helps to retain the insecticide in the pad. Heat and pressure, such as supplied by embossing rolls, may be used to densify this edge section. This aspect of the invention also encompasses including an insecticide in a pad and compressing and thermosetting or heat sealing the edges of the mixture of thermoplastic and other fibers regardless of how the remainder of the mixture is formed. The article can then be cut from the thermobonded web or sheet. Also, a pattern of discontinuous or innerconnected spaced apart field bonds may be provided interiorly of the periphery of the article for added strength.

As described below in the detailed description, in accordance with the invention, a wide variety of thermoplastic and other fibers may be included in the insecticide containing mixture which forms the pad, or the core in the case of composite or laminated articles. Without limiting the breadth of the invention, these mixtures may include thermoplastic fibers and wood pulp fibers in varying percentages depending upon the desired application of the material. Also, natural and synthetic staple fibers, such as cotton and rayon fibers may be included in the mixture. In addition, more than one type of thermoplastic fiber may be included in the mixture with some fibers having a melting point higher than the melting point of others. During thermobonding, these latter thermoplastic fibers are not melted, so that they retain their integrity and add to the strength of the resulting article. In addition, these latter fibers may be of a relatively long length in comparison to the other fibers for additional strength. Bicomponent thermoplastic fibers may also be included in the mixture. In addition, to enhance the blending and degree of thermobonding, wood pulp fibers may be included in the mixture which are on average generally either shorter than, or longer than, the thermoplastic fibers.

Also, the basis weight, taber stiffness, bulk and other characteristics of the pet pads can readily be controlled. For example, the amount of the thermobonded mixture included within the article is easily varied to adjust the basis weight. In addition, the percentage of the surface area of the field of the article which is bonded can also be varied. In accordance with the present invention, articles having extremely high basis weights and loft can be produced. These articles exhibit a high degree of tensile strength, including in the Z direction.

As a further aspect of the present invention, one or more cover layers may be included with the core to provide a composite article. These cover layers may comprise thermoplastic sheet materials or webs which are thermobonded to or otherwise secured to the core. In one illustrated embodiment which is particularly well suited for a mat for a dog, the core forming fibers and an insecticide are deposited on a nonwoven thermoplastic facing sheet as it travels along a foraminous belt or screen. The core and facing sheet are heated to a bonding temperature sufficient to thermobond the core fibers to themselves and to the facing sheet. The integrity of the facing sheet is maintained because it has a higher melting point than the bonding temperature. A liquid impermeable backing sheet is then secured to the surface of the core opposite the facing sheet to provide a composite structure. Field bonds may be provided in the article either before or after the backing sheet is in place. The composite structure is compressed and heat sealed along the eventual peripheral edge margin of the article and then cut as explained above. The backing sheet may be adhesively or otherwise secured at every point of contact to the core or may simply be secured at the field and peripheral bond areas. In addition, the backing sheet may be secured in place after the densified edge margin is formed. In this latter case, the backing sheet is not densified at the edge margin but is otherwise secured in place, as by adhesive.

As a still further aspect of the present invention, the field bonds may be formed prior to, simultaneously with, or following the densification of the edge margin of the articles. Although other approaches are suitable, preferably one or more embossing rolls are used to form the field and edge bonds. When a composite thermobonded core facing sheet is provided with field and edge bonds, the embossing rolls are preferably held at a temperature below the melting point of the thermoplastic materials of the core so as to minimize any delamination of the core and facing sheet. In addition, it has been found that a reduction in shrinkage results if the field bonds are provided prior to the peripheral edge margin bonds of an article.

Accordingly an object of the present invention is to provide improved thermoplastic containing and insecticide containing pet pads and improved methods for forming these pet pads at a cost effective and high volume rate.

Another object of the present invention is to provide pet pads which are economical enough to be disposable upon becoming soiled.

Still another object of the present invention is to provide strong insecticide containing pet pads formed of thermoplastic and other fibers and in particular to provide such articles with edge sections of enhanced tear strength and which minimize leakage.

A further object of the present invention is to provide materials and methods of efficiently manufacturing pet pads from thermoplastic and other fibers which have readily controlled and variable characteristics, such as varying bulks and basis weights.

Still another object of the present invention is to provide pet pads of thermoplastic materials and insecticides which minimize the leakage of liquids, dust and insecticide from the edges of such articles.

These and other objects, features and advantages of the present invention will become apparent with reference to the following detailed description and drawings.

BRIEF DESCRIPTION OF THE DRAWINGS

FIG. 1 is a schematic side elevational view of one form of apparatus for carrying out the present invention;

FIG. 2 is a schematic side elevational view of an alternate embodiment of a portion of the apparatus of FIG. 1;

DETAILED DESCRIPTION OF THE PREFERRED EMBODIMENTS

General Description of Materials

Thermoplastic Fiber Containing Core

Figure 3:
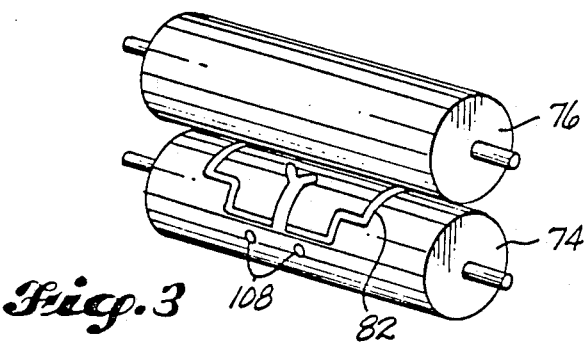
FIG. 3 is a perspective view of a pair of embossing rolls utilized in compressing and heat sealing the peripheral edges of a pet pad made in accordance with the present invention.

Pet pads in accordance with the present invention may be manufactured from a variety of thermoplastic containing materials. Mixtures of thermoplastic fibers and other fibers are particularly well suited and will first be described. Many of the materials are economical enough that they can be used in general for disposable pet pads.

For purposes of convenience, the thermoplastic fiber containing layer will be referred to herein as a core. However, it will be appreciated that in single layer articles or two layer laminated or composite articles, the core itself respectively comprises the article either alone or with the other layer. Thus, in such cases the core would not be sandwiched between two or more cover layers.

As previously mentioned, the core is formed from a mixture of at least one thermoplastic material in fiber form in combination with one or more other fibers. These other fibers may, and preferably do, include wood pulp fibers.

Suitable thermoplastic fibers are typically made from thermoplastic polymers and are commercially available. These thermoplastic fibers have a high surface area to diameter ratio and are capable of melting when subjected to heat. Representative thermoplastic fibers are made from polyethylene, polypropylene, copolymers of ethylene and propylene, and copolymers of propylene and other 1-olefins such as 1-butene, 4-methyl-pentene-1, and 1-hexene. Grafted polyolefins pulps may also be used, in which maleic anhydride or styrene groups are grafted. In some embodiments, the thermoplastic fibers are composed solely of one type of thermoplastic. In other embodiments, they are composed of mixtures of two or more types of thermoplastic fibers. Bicomponent fibers, such as comprised of polyethylene and polypropylene, may also be used. Polyester fibers are still another example of suitable fibers. Cellulose acetate is a further example of a suitable fiber.

Suitable commercially available products for making the thermoplastic fibers include Pulpex ® E-338 from Hercules, Inc., a polyethylene based product; Kodel ® from Eastman Kodak Corporation, a polyester based product; and Vinyon ® from Celanese Corporation.

The thermoplastic materials may also be comprised of a mixture of more than one type of thermoplastic fibers, such as polyethylene and polyester fibers. In this case, during thermobonding, the core is heated to a temperature sufficient to melt the lower melting point thermoplastic fibers (polyethylene) without melting the higher melting point thermoplastic fibers (polyester). Consequently, the integrity of these latter fibers is preserved and strengthens the resulting core. In addition, by making the polyester fibers of a relatively long length, such as equal to or greater than about one-half inch, cores of enhanced tensile strength are produced. This helps these cores to stand up to adverse conditions encountered when used in a pet pad. Typically, in these mixtures the lower melting point thermoplastic material is included in an amount of from about 5%–85% by weight, the higher melting point thermoplastic material is included in a weight percentage of about 1%–15% by weight, and other fibers, such as wood pulp, make up the remainder of the mixture.

As previously mentioned, the fibers mixed with the thermoplastic fibers to form the core may include wood pulp. Wood pulp fibers can be obtained from well known chemical processes such as the kraft and sulfite processes. In these processes, the best starting material is prepared from long fiber coniferous wood species, such as pine, douglas fir, spruce and hemlock. Wood pulp fibers can also be obtained from mechanical processes, such as ground wood, refiner mechanical, thermomechanical, chemimechanical, and chemithermomechanical pulp processes. Recycled or secondary wood pulp fibers and bleached and unbleached wood pulp fibers can be used. Details of the production of wood pulp fibers are well known to those skilled in the art. These fibers are commercially available from a number of companies, including Weyerhaeuser Company, the assignee of the present application.

In addition to wood pulp fibers, other nonthermoplastic synthetic and natural staple fibers such as rayon, cotton and the like may be included in the core forming mixture.

By making the other fibers of the mixture, such as the wood pulp fibers, either shorter on the average or longer on the average than the thermoplastic fibers, when blended the fibers of the mixture tend to become entangled to a greater extent. Therefore, upon thermobonding and melting of the thermoplastic fibers, greater contact between the thermoplastic and other fibers is achieved and stronger bonds are produced.

The optimal amount of thermoplastic and other fibers for a particular blend depends upon the bond strength and other properties desired in the final absorbent core. For cores intended to absorb aqueous based substances, thermoplastic fibers in an amount of from 5%-40% by weight and other fibers such as wood pulp in an amount of about 95%-60% by weight are suitable. In particular, blends of 80% wood pulp fibers and 20% Pulpex® have proven to be preferred. In contrast, a greater oil absorbency is achieved by increasing the thermoplastic fiber content of the mixture. For pads or cores in which this characteristic is desired, blends of thermoplastic fibers in an amount of approximately 95%-60% by weight and other fibers such as wood pulp in an amount of about 5%-40% by weight are desired.

Also, insecticides are either added to the mixture or otherwise included in the pad as explained below. After the mixture is thermobonded, these added materials are substantially retained in place due to the thermobonding. Therefore, the tendency of these materials to escape or migrate from the article and into the external environment is reduced. Materials are selected which do not substantially degrade when subject to the temperature conditions that are present during thermobonding. Also, by selecting thermoplastic materials with relatively low melting points, thermobonding can be accomplished at temperatures which minimize the possible thermal degradation of these materials. Among the suitable insecticide materials that may be included in the mixture are flea and tick powder, such as Carbaryl (1-naphthyl N-methylcarbamate). Another suitable insecticide is Rotenone. A further example is a bird mite and lice insecticide, such as pyrethrins 0.09% by weight, piperonyl butoxide 0.18% by weight, and N-octyl bicycloheptene dicarboximide 0.3% by weight. In addition, deodorizing materials such as oder absorbing, oder masking, oder inhibiting and oder eliminating materials may be included in the core forming mixture. Examples include baking soda, cedar oil and other fragrances. Again, the thermobonding of the core helps fix these materials in place.

While not structurally as strong, it is also within the scope of the present invention to include these insecticides within coform cores formed in the manner described in U.S. Pat. Nos. 4,650,481 of O'Connor et al. and 4,609,580 of Rockett et al.

Instead of including these materials in the core forming mixture prior to bonding, they may be placed on one or both surfaces of the core following the core formation. Although not as advantageous, these materials may be included in an adhesive coating on the core or simply sprayed on the core in liquid form and allowed to dry.

Finally, due to the methods of forming cores for pet pads of the present invention, pet pads of widely varying basis weights may be manufactured.

Facing Layer Materials

In the case of an article formed of the core together with one or more other layers, for convenience one of these layers will be referred to as a facing or first covering layer.

The facing layer typically comprises a preformed sheet or web of material which travels toward a thermobonder. The facing sheet may be of a nonwoven thermoplastic containing material. The core forming mixture is deposited on the facing sheet to the desired depth. To prevent melting of the facing sheet during thermobonding, the facing sheet is selected to have a melting point which is higher than the melting point of the thermoplastic fibers of the core which are to be melted during thermobonding. When the facing sheet and deposited mixture pass through the thermobonder, the core fibers are thermobonded together and to the facing sheet. Of course, the facing sheet can be secured to the core following the formation of the core.

Thus, the selection of the facing sheet material will depend at least in part upon the thermoplastic fibers included in the core. Representative facing sheet materials include thermoplastic coated materials such as rayon resin or otherwise coated with a thermoplastic layer, polyolefin materials, spun laced polyester and polypropylene, resin bonded polyester and polypropylene, spun bonded polyester and polypropylene, thermobonded polyester and polypropylene, carded polyester and polypropylene, melt blown polypropylene, polyethylene films of varying densities, polypropylene films, apertured films and other suitable materials apparent to those skilled in the arts.

In addition, if the illustrated manufacturing method is employed wherein heated air is pulled through the core and the facing sheet during thermobonding, the facing sheet must be perforated or otherwise breathable. Some commercially available suitable nonwoven continuous filament products include Cerex® a nylon material from James River Corporation, Reemay®, a spun bonded polyester material from Intertec Corporation, and Sontara®, a spun laced polyester product from DuPont Corporation. Reemay® would be particularly durable for pet pad applications.

Again, a wide variety of facing sheet materials may be used. These facing sheets may be thermoplastic or thermoplastic containing for those applications in which the facing sheet is to be thermobonded to the core. If the facing sheets are secured to the core in another manner, such as by adhesive, then they need not be thermoplastic. Nonwoven materials are exemplary facing sheets because such materials readily allow the passage of liquids to the absorbent core.

Backing Layer Materials

Again, for convenience, the layer of material on the opposite side of the core from the facing layer will be referred to as a backing or second cover sheet.

The backing sheet may be identical to the facing sheet and may be secured to the core during the thermobonding step. However, the backing sheet may also be comprised of a film having a melting point which is below the melting point of the thermoplastic fibers of the core which are melted during heat fusing of the core. In such a case, these materials may be secured to the core following the thermobonding step.

Also, the backing sheet materials may comprise thermoplastic materials so as to permit thermobonding or thermosetting of the backing sheet along the eventual peripheral edge margin and at field bond areas of the article. Also, the backing sheet may comprise a liquid impermeable material which assists in containing liquids absorbed by the core and through the facing sheet.

Suitable backing sheet materials include, in addition to those mentioned above in connection with the facing sheets, films of polyethylene, polypropylene and polyester and blends of these materials, linear low density polyethylene films, nylon and polyvinylchloride films. An example of a commercially available suitable film is Saran ® from Dow Chemical Corporation.

Thus, a wide variety of suitable materials may be used in the manufacture of thermoplastic containing pet pads in accordance with the present invention.

Manufacturing Method

In a typical approach, the thermoplastic, other fibers, and insecticides to be used in forming the core are blended by any of the known blending methods. Such methods include the preparation of a pulp sheet by conventional paper-making procedures or by conventional dry blending methods. The resulting sheet is then rolled up to form a roll of core forming fibers such as indicated at 10 in FIG. 1. A sheet 12 is fed from roll 10 to a fluff preparation zone 14. At zone 14, the web 12 is formed into a fluff pad by conventional methods such as hammermilling or air forming.

In other suitable approaches, the thermoplastic core forming fibers may be fluffed separately from the other fibers, deposited in a hopper 16, and distributed by an air stream into the fluff preparation zone. In this case, the wood pulp and other fibers are similarly fluffed and deposited in a hopper 18 and distributed by an air stream within the fluff preparation zone for mixing with the thermoplastic fibers from the hopper 16. Insecticide powders may be placed in either hopper. Vacuum air laying techniques may also be employed. Similarly, pulp sheets can be passed through a hammermill with the thermoplastic fibers and insecticides being added in a separate step. Thus, the specific manner of forming the mixture of thermoplastic and other fibers that eventually become the core of the article is not critical.

The core forming fibers may be deposited directly on a foraminous screen 20 with the thickness of the fibers being determined in a conventional manner utilizing a doctor roll. In this case, the screen 20 carries the core forming fibers through a thermobonder 22 which heats the fibers to a temperature above the melting point of at least one thermoplastic fiber material in the core. For example, the melting point of some types of polyethylene pulp is 122° to 134° C. while the melting point of some types of polypropylene fiber is 160° to 165° C. This heat fuses the core. Although calenders, infrared heaters, and other heating devices may be employed to heat fuse the core, the illustrated thermobonder 22 comprises a flow-through dryer. The exact heating conditions, which can be readily ascertained by one skilled in the art, must be determined for the specific fiber blend being used. The time that the core spends within the thermobonder 22 is also readily ascertainable by one skilled in the art. Generally this time ranges from about one hundred milliseconds to one minute depending in part upon the temperature of the thermobonder and the line speed at which the screen is traveling. Thereafter, the core can then be densified at eventual edge margin sections of an article to be formed from the core and otherwise processed as explained below in connection with composite or laminated articles.

In the illustrated embodiment, a thermoplastic containing face sheet, such as a breathable, nonwoven, liquid permeable facing sheet web 24 from a roll 26, is positioned on screen 20 upstream from the fluff preparation zone 14. As facing sheet 24 passes through the fluff preparation zone, the core forming fibers and insecticides are deposited on the facing sheet to the desired depth. The unfused core forming fibers, indicated at 28 in FIG. 1, together with the facing sheet 24, are carried by the belt 20 into the thermobonder 22.

Although not required, the thermobonder has three stages 30, 32 and 34. In each stage, heated air enters from a respective inlet 36, 38 and 40. The entering heated air passes successively through the core forming fibers 28, the facing sheet 24, the belt 20 and to a respective exit outlet 42, 44 and 46. A pressure differential is maintained across the traveling materials to draw the heated gas through these materials. For example, the inlets may be pressurized relative to the outlets or a vacuum may be applied to the outlets. The melted thermoplastic material fibers of the core 28 fuse or thermobond the core to itself and also to the face sheet 24. The temperature is such that the face sheet 24 is not melted by the thermobonder 22. Protection of the face sheet from melting is enhanced by passing heated air through the core and then to the facing sheet.

Typical line speeds for the screen 20 are from 100 to 250 feet per minute with 150 feet per minute being a normal operating speed. The thermobonder 22 includes an optional convection oven or apron 50. This oven maintains the temperature of the bonded core and facing as these materials travel toward a feature forming zone 54.

In a first approach illustrated in FIG. 1, a backing sheet 56, which may be of a thermoplastic containing liquid impermeable material, is fed from a roll 58 to the exposed surface 60 of the core.

At feature forming zone 54, the multilayered or composite web is bonded or densified along at least a section of the eventual peripheral edge margin of an article to be formed. Typically, the entire eventual peripheral edge margin of the article is densified at this time. In addition, optional field bonds may also be formed within the eventual field of the article intermediate the peripheral edge margin.

A number of suitable processes may be used to form these densified areas. These include ultrasonic bonding and adhesive bonding. However, the preferred approach is to emboss these bond areas. To this end, opposed sets of embossing rolls 70, 72 and 74, 76 are positioned as shown. The illustrated roll 70 comprises a field bond feature forming roll having a projecting pattern of field bond forming contacts 80 which press against the face sheet and other layers of the composite material. Roll 72 comprises a smooth surfaced anvil roll which is positioned against the backing sheet 56. Similarly, roll 74 comprises a peripheral edge margin feature forming roll having contacts 82 arranged to define those sections of the eventual peripheral edge margins of the article which are to be densified. Normally, the entire eventual edge margin of the article is densified by feature forming roll 74. Roll 76 comprises a smooth anvil roll which backs up the feature forming roll.

A conventional temperature control 90, 92, 94 and 96 is provided for each of the respective rolls 70, 72, 74 and 76 for independently controlling the temperature of these rolls. If the same materials are being used for the backing and facing sheets, typically these rolls are kept at the same temperature. Also, the temperature is held at a level which permits thermobonding of the core materials being used without thermally breaking down the insecticide. If the rolls are held at temperatures below the melting point of the thermobonding temperature of the core, the rolls are typically of 120°–130° C., depending upon the materials. In cases where the backing sheet 56 has a relatively low melting point, rolls 72 and 76 may be kept somewhat cooler (i.e. at 80°–110° C., depending upon the material) than rolls 70 and 74 to act as a heat sink to assist in cooling the backing sheet 56 below its melting point.

The temperature of the embossing rolls 70 through 76 is preferably held cooler than the melting point temperatures of both the core 28 and the face sheet 24. By maintaining the core 28 above its thermobonding temperature when it reaches the embossing rolls, the feature forming rolls bring the core below the thermobonding temperature to thermoset or heat seal and compress the peripheral edge margins and field bonds in the pad or other article. Also, the core and face sheet do not tend to delaminate when embossed with these cooler embossing rolls. This helps to control the shrinkage of the article during embossing.

The field bond contacts 80 and peripheral edge margin bond contacts 82 may be placed on the same roll. When articles from some of the above described materials were made in this manner, greater shrinkage of the article resulted than when the field bonds were provided before the edge margin bonds. The peripheral bonds can be provided ahead of the field bonds. However, the preferred results were obtained when the field bonds and peripheral edge margin bonds were provided at successive embossing locations. When formed first, the field bonds reduced shrinkage and tended to keep the layers of the composite material from shifting and bunching or gathering at the peripheral edge margins of the article.

Figure 8:
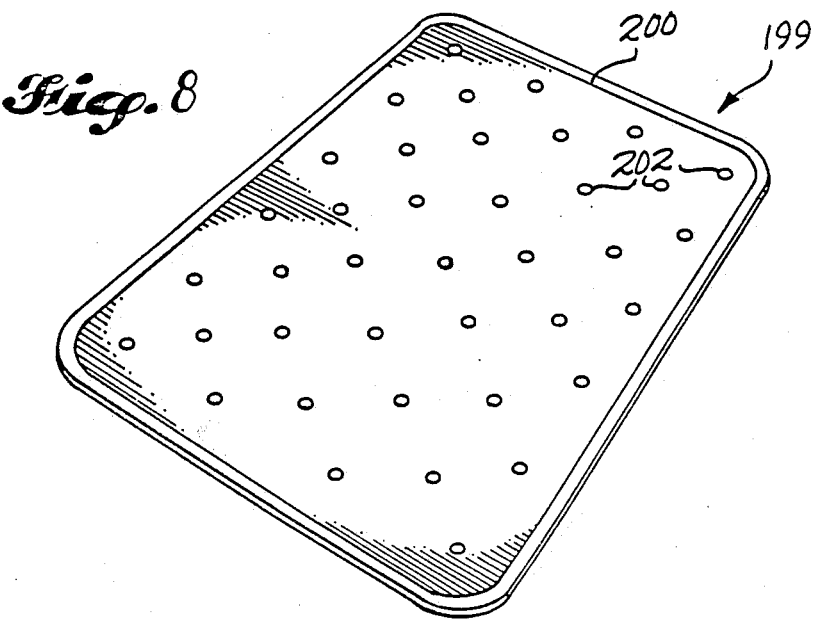
FIG. 8 is a perspective view of another pet pad in accordance with the present invention.

A feature roll 74 and anvil roll 76 for densifying the eventual peripheral edge margin of the pet pad of FIG. 8 is shown in greater detail in FIG. 3.

The nip gap between the contacts 80 and 82 and the corresponding anvil rolls is typically from about two to twelve thousandths of an inch with four to eight thousandths of an inch being preferred. Bond strength significantly decreases with a gap distance above twelve thousandths of an inch. In addition, the depth between the contact and relief portions of the feature rolls 70, 74 is sufficient to accommodate thick materials. Typically one-quarter inch to one-half inch spacing is provided between the contact and the relief portions of these rolls. Consequently, high loft, deep relief products can be produced using the FIG. 1 apparatus. Embossing pressures are variable, depending upon the desired density of the bonded areas, with 1,000 psi to 5,000 psi embossing pressures being typical.

The field embossed patterns typically comprise spaced apart embossed areas such as dots or intersecting lines. For higher bulk products, fewer field embossed areas are provided. Typically, no more than about 2%–4% of the surface of the article is embossed with field patterns. However, for some applications, additional embossing may be provided.

The Z direction tensile strength of articles formed in this manner is enhanced by the embossed areas. In addition, by embossing all or sections of the eventual peripheral edge margins of the article, the tensile strength of the article in X, Y and Z directions is substantially improved, especially at the edge. In addition, a densified peripheral edge margin impedes the leakage of liquid from the pad through the edge.

Following embossing, the articles may be separated from the composite material. Although the articles can be separated in the manufacturing line following embossing, in the illustrated embodiment the articles are separated from the composite materials at a cutting location separate from the line. A laser, die, waterknife or other cutting mechanism 100 is used to separate the composite materials into pads 102 which contain the articles defined by the peripheral edge margins embossed thereon. The separated pads 102 are then stacked in a bin 104 for subsequent transportation to a cutting zone where the finished articles are severed from the pads.

As shown in FIG. 3, optional pin register defining contacts may be included on feature roll 74. These contacts form corresponding bonds on the individual pads 102. These latter bonds may be registered with optional pins 110 of bin 104 so that the individual pads 102 are aligned in the bin. More than one of the aligned pads can then be cut at a time at the cutting location with the pads being held in position by pins inserted through the bonds defined by contacts 108. Other pad alignment mechanisms can also be used. Also, individual pads may be cut rather than cutting the pads in stacks.

For articles with a backing sheet 56 of materials like those of face sheet 24, the backing sheet may be added to the composite material upstream of the thermobonder 22. This is shown by the roll 58 and sheet 56 depicted in dashed lines in FIG. 1. Also, the facing sheet 24 may be added following the passage of the core through the thermobonder 22. This is shown by the sheet 24 and roll 26 illustrated in dashed lines in FIG. 1. In this case, the bond between the face sheet 24 and core is not as strong as when both the core and face sheet pass through the thermobonder. Adhesive binders may be used to strengthen the bond between the face sheet and core if this approach is used.

In addition, an adhesive applicator, shown in dashed lines at 114 in FIG. 1, may be used to apply an adhesive coating to the surface 60 of the core or directly to the backing sheet ahead of the application of backing sheet 56 to the core. This adhesive serves to secure the backing sheet to the core at every point of contact between the backing sheet and core. This increases the strength of the composite material over the case where field and peripheral bonds are the only means of securing the backing sheet in place.

In the approach illustrated in FIG. 2, the embossed thermobonded facing sheet and core is passed through a cooling chamber 120. In chamber 120, cool air is passed from an inlet 122, around the thermobonded facing sheet and core and to an outlet 124. Thereafter, adhesive is applied by applicator 114 to the surface 60 of the core. The backing sheet 56 from roll 58 is then positioned on this adhesively coated surface. The assembled composite material is then optionally pressed between a pair of rolls 126, 128 to ensure a secure bond between the backing sheet 56 and core at every point of contact between these components. Thereafter, the individual sections 102 of the material are singulated as previously described. With this approach, backing sheets of extremely low melting points may be mounted to the core without being melted by the core and while permitting high line operating speeds. In addition, glues or adhesives may be used that otherwise could be degraded by heat from the core. The adhesively secured backing sheets not only strengthen the composite material when bonded at every point of contact as previously mentioned, but also prevent propagation of tears in the backing sheet.

As another approach, the backing sheet 56 may be placed on the core between the set of field bonding rolls 70, 72 and the set of peripheral edge margin feature forming rolls 74, 76 as shown in dashed lines in FIG. 2. In this case, the sheet 56 from roll 58 is embossed at the eventual peripheral edge margin of the article but not at the field bond locations. Again, adhesive may be applied, as indicated by the applicator 114 shown in dashed lines, to the surface 60 of the core upstream of the backing sheet or applied directly to the surface of the backing sheet which is to be secured to the core. Improved bonding is provided at the peripheral edge margin of the article when the backing sheet is passed through the rolls 74, 76 in comparison to applying the backing sheet to the core downstream from these rolls.

Figure 5:
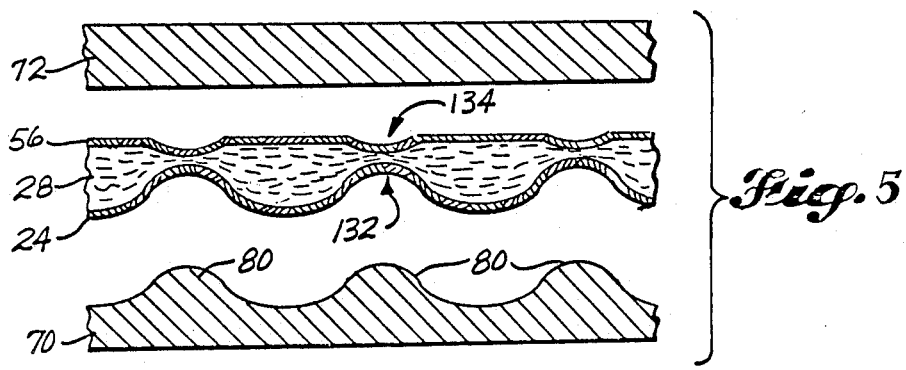
FIG. 5 is a cross-sectional view of an insecticide containing composite material in accordance with the present invention after compression and bonding by embossing rolls.

FIG. 5 depicts the composite core, facing and backing sheets as they leave the space between the rolls 70 and 72 following compression between the contact points 80 of the roll 70 and the corresponding surface of the anvil roll 72. Thereafter, the material passes from the field bond defining rolls 70, 72 to the peripheral edge margin defining rolls 74, 76. As a result of this field bonding, compressed or dimpled areas 132 are provided in the face surface of the composite material. In addition, a slight recess 134 is typically also visible in the backing sheet due to the compression of the backing sheet during field bond formation and as a result of removal of contacts 80 from the facing surface.

Figure 6:
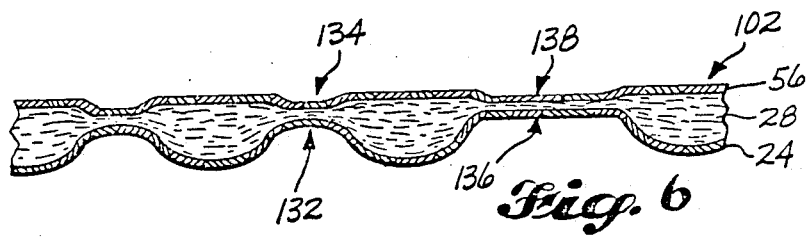
FIG. 6 is a cross-sectional view of an insecticide containing composite material in accordance with the present invention following the formation of field and peripheral edge margin defining bonds of a pet pad.

As can be seen in FIG. 6, following the densification of the eventual peripheral edge margin sections of the article, a densified area 136 remains along the eventual edge margin. Also, a slight depression 138 is present in the backing sheet opposite the depression 136. The edge margin depressions are typically one-quarter to three-eighths inches wide.

Figure 4:
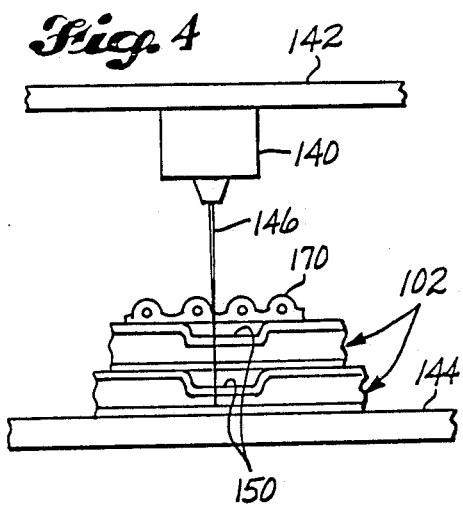
FIG. 4 is a schematic illustration of one form of apparatus used for cutting pet pads of any desired shape.

At the cutting zone, the desired articles are cut from the pad sections 102 by a cutting mechanism such as a die, laser, or water knife or other cutting mechanism. A suitable water knife cutting systems is shown schematically in FIG. 4. Devices using a water knife, sometimes called a fluid jet, for cutting strip-like material are known. U.S. Pat. No. 4,620,466 of Jumel et al. describes one such device. Similarly, a water knife may be used in conjunction with a cutting system sold under the brand name GerberCutter by Gerber Garment Technology, Inc. of South Windsor, Conn. With reference to FIG. 4, a water knife 140 is supported by a computer controlled movable support, such as found in the GerberCutter apparatus or the cutting machine of the aforementioned Jumel et al. patent. One or more pad sections 102 to be cut are positioned on a table 144. The table is capable of moving the pads in a direction perpendicular to the direction that the water knife is moved by support 142. This combination of motions, as described in the Jumel et al. patent and in the analogous GerberCutter system, allows any arbitrary shaped article to be cut from the pad sections 102. As previously described, the pad section 102 may be held in place by optional pin 110 (see FIG. 1). A water stream 146 from water jet 140 severs the articles, typically in a densified area 136 at the periphery of the articles.

Although not shown, two water knives may be mounted to support 142 for cutting articles which are symmetric about a center line from the pad 102. Pet pads of complex shapes may be cut in this manner.

The cutting mechanism may be adjusted to cut the pad 102 to provide a peripheral edge within the densified peripheral edge margin 136 of the pad. Alternatively, the cutting mechanism may be adjusted to cut the peripheral edge margin of the article at a location which is slightly outside of the densified peripheral edge margin 136. For example, the peripheral edge may be approximately one-eighth inch away from the densified peripheral edge margin and outside of the field of the article. In this case, the peripheral edge is located in a relatively undensified area of the article. As a result, the edge will have a softer feel in comparison to the case wherein the cut is made in the densified edge margin. The cut location may be adjusted such that a soft edge is provided at selected locations along the article while a harder edge is provided at other locations. In this latter case, only selected portions of the article would have a soft edge. However, in each case, the densified peripheral edge margin strengthens the article and impedes leakage of urine and liquids through the densified edge margin to the periphery of the article.

Figure 7:
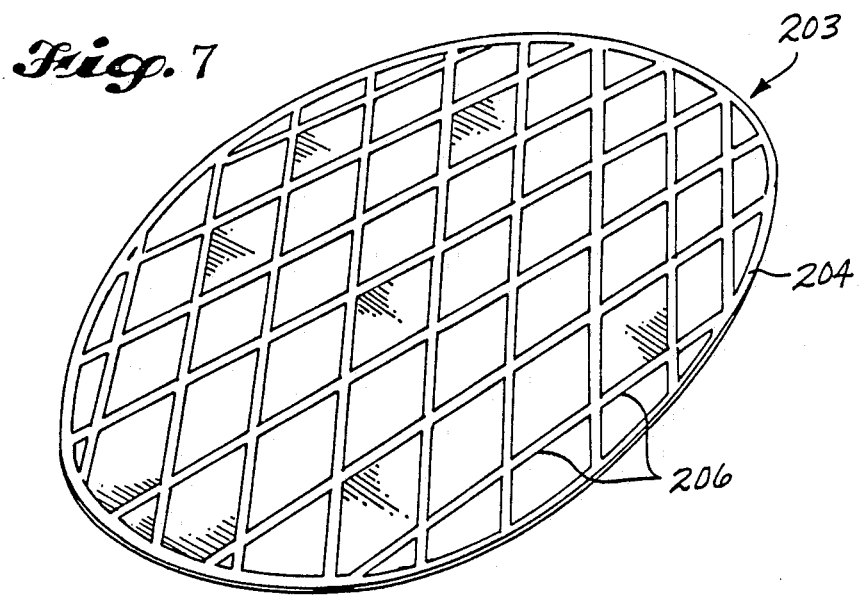
FIG. 7 is a perspective view of a pet pad or mat in accordance with the present invention.

FIGS. 7 and 8 illustrate examples of pet pads manufactured from the materials of and in accordance with the methods of the present invention. In connection with these and other examples, the various characteristics and properties of the thermobonded cores and of the composite articles referred to herein, and throughout the detailed description, are measured by the methods listed in Table I. In this table, ASTM refers to the American Society of Testing Materials and Tappi refers to the Technical Association of Pulp and Paper Industry.

TABLE I

| Characteristics | Property Measurements | |
|---|---|---|
| | Test Method | Units |
| Basis Weight | Tappi T-410 OM | g/m$^2$ |
| Caliper or thickness | Tappi T-411 OS | mm |
| Density | Tappi T-410 OM | g/cm$^3$ |
| Bulk | Tappi T-426 WD | cc/g |
| Machine Direction Tensile Strength | Tappi T-494 | Newtons |
| Cross Machine Direction Tensile Strength | Tappi T-494 | Newtons |
| Z Direction Tensile Strength | Tappi T-506 | KN/m$^2$ |
| Taber Stiffness | Tappi T-489 | g-cm |
| Liquid Capacity | ASTM-D 535 | ml/g |
| Elmendorf Tear | Tappi T-414 | Newtons |

EXAMPLE 1

In this first example, a single layer article or pad was formed by thermobonding a uniformly mixed blend or mixture of thermoplastic and other fibers of the type having a high surface area to diameter ratio. More specifically, Pulpex ® E-338 from Hercules Corporation in an amount of 20 percent by weight of the article was mixed with 80% by weight of wood pulp fibers. The specific wood pulp fibers utilized in this example were NB-316 fibers available from Weyerhaeuser Corporation. This Pulpex ® is comprised of fibers having a diameter of greater than approximately 9 microns. Fibers of this type have a greater average surface area than typically found in the case of microfibers used in coform processes. Consequently, stronger bonding results. Insecticides, such as lice and mite insecticides for birds, can be included in this mixture as previously mentioned.

The mixture was deposited on the moving screen 20 (FIG. 1) and passed through the thermobonder 22, within which the thermoplastic fibers were melted to fuse the core. This would also fuse or fix insecticide powders in the core. The thermobonded core was also passed through a peripheral edge margin defining feature roll which densified the entire eventual edge margin of the article. The density at the densified edge margin has been tested (without the insecticide) at 0.3 to 0.6 g/cm$^3$ and typically can be from about 0.3 to 1.0 g/cm$^3$. The Z direction tensile strength of the pad is anticipated to be the same as the Z direction tensile strength of a multilayered pads. Thus, the dry tensile strength has been tested at 58.1 KN/m$^2$ at the densified edge margin while the wet tensile strength has been tested at 25.7 KN/m$^2$ at this location for an article with an edge margin of a density at 0.3 g/cm$^3$. Comparable results are expected when the insecticide is included. Higher tensile strengths are expected for cases where the density of the edge margin is higher.

EXAMPLE 2

This example is like Example 1 with the addition of field bond areas within the field of the article. These field bond areas are spaced apart and may comprise point bonds, quilted pattern bonds, or other bond configurations. Typically, the field bonds occupy two to four percent of the surface area of the article. Pads of this type without insecticide and with widely varying basis weights have been manufactured in accordance with the present invention. The basis weights of pads made in this manner has ranged from eighty to seven hundred fifty g/m$^2$. In addition, by varying the quantity of the field bonds and the basis weight, pads of varying taber stiffness can be produced, such as ranging from ten to one hundred g-cm. It is expected that these characteristics can also be obtained in the core when insecticide is also added.

At the densified edge sections of the pad, the pad resists dusting or the loss of fibers at the edge and also resists leakage of liquid through the edge. Also, a pad with a densified edge has a good Z direction tensile strength, such as described in connection with Example 1, can be obtained.

EXAMPLE 3

Insecticide containing articles formed of thermoplastic and other fibers held together by latex bonds or coformed and provided with a thermobonded edge in accordance with the present invention also would exhibit the desired characteristics at the edge of the articles. However, in the case of coform, the Z direction tensile strength of such articles would be weaker in the body of the articles. Also, the densified edge is also somewhat weaker unless the edge is thermobonded, such as when the core is thermobonded or when the densified edge is formed. In addition, latex can coat insecticide powder and reduce its effectiveness.

Also, odor absorbents such as baking soda or deodorizers such as cedar oil can be added to the core forming materials. Cover sheets, including those containing thermoplastic materials thermobonded to the core may also be used to enclose the cores formed in this manner. Alternately, these materials may be coated or applied as a layer on the core and held in place by adhesive and a cover layer. However, it is preferred to thermobond these materials within the core as this more effectively fixes or retains them in place.

EXAMPLE 4

This example is like Example 1 except that an insecticide, such as flea powder, can be added to or coated on the core. By including this material within the thermobonded core mixture, migration of the material into the environment is minimized. Moreover, the life of a thermobonded core with flea powder is expected to be longer due to the retention of the flea powder in place. Cores or pads treated in this manner are suitable for pet blankets and the like. Again, cover sheets, including thermoplastic containing cover sheets, may be thermobonded or otherwise secured to the cores.

EXAMPLE 5

In this example, the core is comprised of 20 percent Pulpex ® and 80 percent wood pulp fibers. In addition, a facing sheet of a non-woven liquid permeable thermoplastic material, in this case polypropylene, was used and a liquid impermeable backing sheet film, in this case polyethylene film, was used.

During manufacture of an article for other than a pet pad use, the core was thermobonded to itself and also to the face sheet in the thermobonder 22 (FIG. 1) at a temperature of about 140°–145° C. for about five seconds. The dwell time in the thermobonder is typically increased for increasing basis weight cores. In addition, the face sheet and core were thermoset together at field regions within the article and all three layers were thermoset at the eventual peripheral edge margin of the article by feature forming embossing rolls at about 120°–130° C. and anvil embossing rolls at about 80°–110° C. The article was then cut in the densified areas. The basis weight of these articles varied from 80 to 450 g/m$^2$. The taber stiffness of such articles can be adjusted from 10 to 100 g-cm.

One specific article constructed in this manner had a basis weight of 229.5 g/m$^2$ at its densified edge, a caliper of 0.763 mm at the edge and an edge density of 0.305 g/cm$^3$. The tensile strength of this article at the compressed edge area of the liner in the Z direction was 58.1 KN/m$^2$ when dry and 25.7 KN/m$^2$ when wet. The density at the compressed edge area of such article typically can be varied from 0.3 to 1.0 g/cm$^3$. In addition, although variable, the field bonds of such material can occupy an area of from about 2 to 4 percent of the entire surface of the article.

In addition, the absorbency capacity of these articles has been tested at typically 10 to 16 ml/g of material. The wicking rate of such articles can vary from 5 to 25 ml/minute depending upon the pad construction. In addition, the tested edge wicking in ml/minute was virtually 0 in the densified edge areas for articles tested with edge densities of about 0.5 g/cm$^3$.

Pet pads with insecticides included in the core can be cut from this type of material and would exhibit the above characterics. Pet pads with a basis weight in the range set forth above would provide good cushioning, excellent thermal insulation, good absorbency and adequate flexibility.

The tear resistance of such pads (determined in accordance with TAPPI T-414) in the machine direction would vary from about 1,000 mN when no glue is used to secure the backing sheet and the backing sheet was thermoset in place to about 4,000 mN when glue is used and the backing sheet was not thermoset to the core. This tear resistance is largely a function of the thickness of the backing sheet and the temperatures to which the backing sheet has been subjected. The ratio of the wet tensile strength to the dry tensile strength of the total pad (determined in accordance with TAPPI T-494) can vary from about 0.5 to 1.0 with the same approximate ratio being present in both the machine and cross machine directions. In addition, the Z direction tensile strength of the pad without glue being used for securing the backing sheet in place, and excluding the densified regions of the pad, can vary from about 1 to 5 KN/m$^2$.

Articles in accordance with this construction have been folded and unfolded over 5,000 times without failing. Pet pads of this construction are expected to be disposable.

EXAMPLE 6

This example is like Example 5 except that the backing sheet is secured in place by intermediate field bonds either with or without the adhesive. The use of field bonds and peripheral bonds would increase the Z tensile strength of the composite article. However, the difference would not be noticeable to any significant extent if adhesive is also used to secure the backing sheet in place.

EXAMPLE 7

This particular example relates to the pad 199 shown in FIG. 8 which is generally of a rectangular shape. The peripheral edge of the pad is densified at 200. In addition, point field bonds 202 are provided throughout the field of the pet pad. These field bonds are about 2 inches apart. The overall size of the illustrated pad is 9½ inches by 16½ inches.

This pad has a core formed of 20 percent Pulpex ® and 80 percent wood pulp fibers. In addition, a 0.7 ounce/yard nonwoven thermoplastic material, in this case APN 185 carded thermobonded nonwoven polypropylene can be provided as the facing and backing sheets. The facing and backing sheets are thermobonded to the core and heat sealed or thermoset at the edges.

The basis weight of the pad can be approximately 175 g/m$^2$, the density of the pad is approximately 0.05 g/cm$^3$, the taber stiffness of the pad is about 5 to 6 (and more specifically 5.4) g-cm, the thickness of the pad is about 4 mm, and the absorbency of the pad is about 10 to 15 ml/g. Insecticides, such as bird mite and lice insecticide, may be included in the core of this pad. The pad can then be used as a cover or liner for bird cages. However, for some insecticides, the pads must be placed in a location where they are inaccessible by the birds.

EXAMPLE 8

This example, relates to the pet pad or mat 203 shown in FIG. 7. The mat of this example was constructed of a core comprised of 80 percent wood pulp fibers and 20 percent Pulpex ®. Facing and backing sheets comprised of 1 ounce/yard$^2$ APN 185 nonwoven thermoplastic material was used. The facing and backing sheets were thermoset to the core and densified at the periphery 204 of the mat.

The basis weight of this mat is variable, and is typically greater than 500 g/m$^2$. A specific example of this mat had a core basis weight of approximately 700 g/m$^2$. The thickness of this mat was about 12.7 mm and the density of this mat was approximately 0.05 g/cm$^3$. The taber stiffness of this mat was approximately 250 g-cm, more specifically 254 g-cm.

The field bond areas 206 of this example pad comprise a crosshatched spaced apart diamond pattern formed of parallel bond lines extending in a first direction which are intersected by parallel bond lines extending in a second direction. The parallel lines forming this pattern are about one inch apart. The overall dimensions of the illustrated mat 203 are about 34 inches long and 24 inches wide. Although other field bonding patterns may be used, field bond patterns which form compartments within the pad surface keep the core material of the mat from shifting in the unlikely event the core material separates from the cover sheets. Flea powder can be included in the core of this mat.

Therefore, in accordance with the present invention, a wide variety of insecticide containing pet pads of varying shapes and characteristics can readily be formed from thermoplastic and other fibers.

Having illustrated and described the principles of our invention with reference to a number of preferred embodiments, it should be apparent to those of ordinary skill in the art that such embodiments may be modified in detail without departing from such principles. We claim as our invention all such modifications as come within the true spirit and scope of the following claims.

We claim:

1. A pet pad having a body with a field bounded by a peripheral edge margin and a peripheral edge, the body comprising a thermobonded mixture of thermoplastic containing fibers, other fibers and an insecticide.

2. A pet pad according to claim 1 in which the insecticide comprises flea powder.

3. A pet pad according to claim 1 which is densified at the peripheral edge margin and at field bond locations within the field of the body.

4. A pet pad having a body with a field bounded by a peripheral edge margin and a peripheral edge, the body comprising a thermobonded mixture of thermoplastic containing fibers, other fibers and an insecticide the mixture comprising a core and in which the body has a liquid permeable facing sheet and a liquid impermeable backing sheet mounted to the core.

5. A pet pad according to claim 4 in which the facing sheet is of thermoplastic containing materials compressed and bonded to the core at the peripheral edge margin and at field bond locations within the field of the core.

6. A pet pad according to claim 5 in which the backing sheet is of a thermoplastic containing material which is compressed and bonded to the core of the peripheral edge margin and at field bond locations within the field of the core.

7. A pet pad comprised of a body having a field bounded by a peripheral edge margin and a peripheral edge, the body having a core of thermoplastic containing fibers and other fibers, a facing sheet and a backing sheet, the body also including an insecticide.

8. A pet pad according to claim 7 which is densified and bonded at the peripheral edge margin.

9. A pet pad according to claim 8 which is densified and bonded at field bond locations within the field of the pet pad.

10. A pet pad according to claim 7 which is densified and bonded at field bond locations within the field of the pet pad.

11. A pet pad according to claim 9 which has a liquid permeable facing sheet and a liquid impermeable backing sheet.

12. A pet pad having a body with a field bounded by a peripheral edge margin and peripheral edge, the pet pad comprising a core of a thermobonded mixture of thermoplastic containing fibers, wood pulp fibers and an insecticide, a facing sheet secured to the core and a liquid impermeable backing sheet secured to the core, the core being densified at the peripheral edge margin of the pet pad and at field bond locations within the field of the pad.

13. A pet pad according to claim 12 in which the backing sheet is of a thermoplastic containing material thermobonded to the core at the densified peripheral edge margin and at the field bond locations.

14. A pet pad according to claim 12 in which the facing sheet is of a thermoplastic containing material which is thermobonded to the core at every point of contact with the core and which is densified at the peripheral edge margin and at the field bond locations.

15. A pet pad according to claim 14 in which the backing sheet is of a thermoplastic containing material thermobonded to the core at the densified peripheral edge margin and at the field bond locations.

* * * * *